United States Patent [19]

Myers

[11] Patent Number: 5,771,935
[45] Date of Patent: Jun. 30, 1998

[54] CHECK VALVE, ESPECIALLY FOR THE MEDICAL TECHNIQUE

[75] Inventor: Jan Willem Marinus Myers, Venlo/Holand, Netherlands

[73] Assignee: Filtertek B.V., Ireland

[21] Appl. No.: 781,011

[22] Filed: Jan. 9, 1997

[51] Int. Cl.$^6$ .................................................. F16K 15/14
[52] U.S. Cl. .......................... 137/859; 251/368; 251/61.1; 604/247
[58] Field of Search ........................... 137/859; 251/368, 251/61.1; 604/247, 249

[56] References Cited

U.S. PATENT DOCUMENTS

| | | | |
|---|---|---|---|
| 3,633,605 | 1/1972 | Smith | 137/859 |
| 4,237,880 | 12/1980 | Genese . | |
| 4,241,756 | 12/1980 | Bennett et al. | 137/859 |
| 4,343,305 | 8/1982 | Bron . | |
| 4,534,764 | 8/1985 | Mittleman et al. . | |
| 4,846,215 | 7/1989 | Barree | 137/859 |
| 4,966,199 | 10/1990 | Ruschke . | |
| 5,025,829 | 6/1991 | Edwards et al. . | |
| 5,453,097 | 9/1995 | Paradis | 604/247 |
| 5,520,661 | 5/1996 | Lal et al. . | |
| 5,617,897 | 4/1997 | Myers | 137/859 |

FOREIGN PATENT DOCUMENTS

| | | |
|---|---|---|
| 0 612 537 A2/A3 | 8/1994 | European Pat. Off. . |
| 27 13 618 A | 10/1977 | Germany . |
| 27 13 618 C2 | 10/1977 | Germany . |
| 30 35 301 A | 4/1981 | Germany . |
| 82 14 927 U | 9/1982 | Germany . |
| 32 15 329 A | 12/1982 | Germany . |
| 86 03 917 U | 5/1986 | Germany . |
| 38 03 380 A1 | 8/1989 | Germany . |
| 40 39 814 A1 | 6/1992 | Germany . |
| 41 42 494 A1 | 7/1993 | Germany . |
| 42 01 258 A | 7/1993 | Germany . |
| 93 19 810 U | 3/1994 | Germany . |
| 43 09 262 A | 6/1994 | Germany . |
| 43 04 949 A1 | 8/1994 | Germany . |
| WO 88/02639 | 4/1988 | WIPO . |
| WO 96 03166 | 2/1996 | WIPO . |

*Primary Examiner*—Denise L. Ferensic
*Assistant Examiner*—Joanne Y. Kim
*Attorney, Agent, or Firm*—Brinks Hofer Gilson & Lione

[57] ABSTRACT

A check valve, especially for the medical technique having a first hose connector housing (1) and a second hose connector housing (2) and further a flexible diaphragm disk (3) positioned between the two joined hose connector housings (1, 2). At an overpressure in an entry space (6) the diaphragm disk (3) can be lifted from a lip-shaped sealing ring (13), whereby a flow cross-sectional area is created, and wherein the diaphragm disk (3) at an overpressure in an exit space (7) safely and in minimal times can be pressed onto a sealing seat to close the valve. The circular diaphragm disk (3) is produced from liquid silicone, silicone rubber or natural rubber and the thickness (3c) of the diaphragm cross-section (3a) is uniform.

17 Claims, 2 Drawing Sheets

CHECK VALVE, ESPECIALLY FOR THE MEDICAL TECHNIQUE

FIELD OF THE INVENTION

The invention relates to a check valve, especially for the medical technique having a first hose connector housing and a second hose connector housing and, further, a flexible diaphragm disk positioned between the two hose connector housings and consisting of a flexible material which at a suitable overpressure in the entry space can be lifted from a lip-shaped sealing ring, creating a flow cross-sectional area and which at a suitable overpressure in the exit space safely and in minimal time can be pressed onto a sealing seat to close the valve.

BACKGROUND OF THE INVENTION

A check valve of this kind is known (DE 40 39 814 A1; DE 43 04 949 A1). Check valves of this kind preferably are used in infusion sets in the medical technique. The infusion liquid flows from an infusion bottle via a needle into a drip container and from there via the hose into a proportional controller which can be substituted by a check valve. Downstream the proportional controller usually there is additionally a controller positioned on the infusion hose in the form of a so-called roller clip. Beyond this controller, the infusion hose usually by a tape bandage is introduced into the vein of a patient. The known valves, however, in view of their disclosed structure and/or process of manufacture are not entirely suitable for their intended function.

One reason for the disadvantages of known check valves are their deficiencies caused by the respective method of production. For example, the check valve known from DE 43 04 949 A1 may not be economically mass-produced in such close tolerances that the demanded number of thousand valves completely achieves the function of closing and opening at low pressures. Further, with such known check valves there are problems with regard to the material used.

Additionally, achieving the above-noted functions e.g. with the check valves described in DE 43 04 949 A1, is drastically influenced by the disclosed openings in that the material cannot be manufactured in the necessary uniform thickness for the disclosed diaphragm disk. A further problem is presented by the mounting of such a known check valve. These check valves, which are produced in thousands due to the costs involved, should be mounted by hand to achieve the above-noted function. Therefore there is a need for a check valve that achieves the function of closing and opening at low pressures and is configured to allow for exclusively automated mounting procedures and does not demand a special design and special materials.

SUMMARY OF THE INVENTION

The present invention therefore has the task to create a check valve of the above defined kind which reliably meets the valve function for the stated range of pressures of a fluid flow, as for example of an intravenous infusion of a liquid into a patient, and simultaneously allows for an automated mounting during its manufacture.

This task according to the invention is solved by the features that the diaphragm disk, which is preferably circular, is manufactured from liquid silicone, silicone rubber or natural rubber and that the uniform thickness of the diaphragm cross-section is chosen with a tolerance which is based on the method of producing a silicone, silicone rubber, or natural rubber sheet or mat. Such a diaphragm disk may reliably open and close and the check valve can be manufactured by automated mounting. In this connection, safety against leakage due to fluid flow opposite to the basic direction of the fluid stream for the check valve is provided herein, as discussed more fully below. The uniform thickness of the diaphragm cross-section only is achieved by the above choice of the material.

A further feature of a preferred embodiment of the invention is that the diaphragm disk is circular and has a diameter of about 10 mm and a thickness of about 0.2 to 0.5 mm. In this combination thickness and diameter very advantageously are correlated to each other for a silicone rubber material, for example.

Further, the above-noted task is solved by the features that the diaphragm disk, preferably with an annular margin, overlies a sealing ring, and the disk margin is clamped between a ring-shaped seat of the first hose connector housing and a compression ring of the second hose connector housing in a sealing manner and the first and the second hose connector housings being manufactured from plastics, are preferably directly welded to each other in this relation.

A further feature of a preferred embodiment of the invention is that about the diaphragm disk there is formed an annular valve space and adjacent thereto one or more radial valve spaces, which in combination with one or more compression ring passages provide a channel for fluid. By doing so, the central space or passage is completely free from disturbing construction elements which means that the position of the diaphragm disk is securely defined.

A further feature of a preferred embodiment of the invention is the production of the diaphragm disk as such. It is proposed that the diaphragm disk is stamped or die cut from a sheet manufactured from liquid silicone, silicone rubber or natural rubber or from a mat consisting of silicone or natural rubber in a flat state. By this, the diaphragm disk is neither electrostatically charged nor is it distorted or tensioned. The typical static charging of the diaphragm disk during manufacture is thereby avoided.

Other features and advantages of the present invention will become more fully apparent from the following description of the preferred embodiment, the accompanying drawings, and the appended claims.

DETAILED DESCRIPTION OF THE DRAWINGS AND OF THE PREFERRED EMBODIMENT

Figure 1:
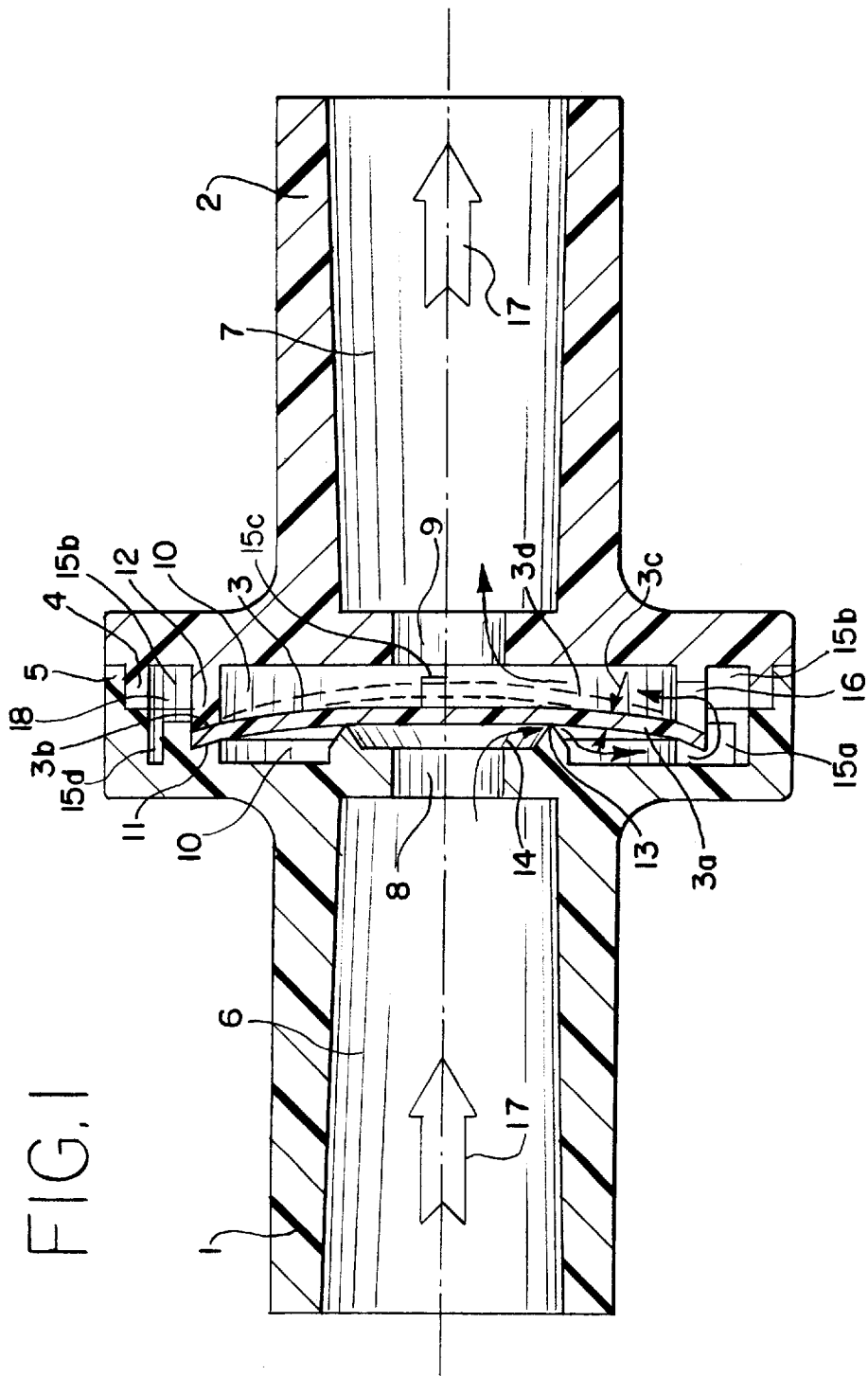
FIG. 1 is an axial longitudinal sectional view of an embodiment of the check valve of the present invention.
Figure 2:
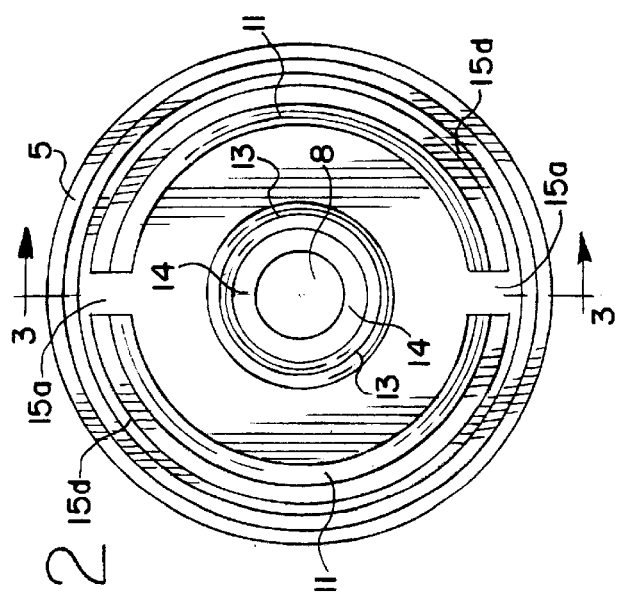
FIG. 2 is a plan view of an embodiment of a first hose connector housing of the present invention.
Figure 5:
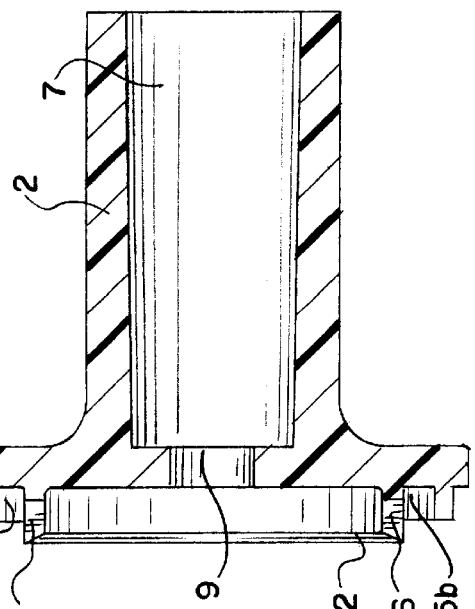
FIG. 5 is a sectional view taken along line 5—5 of FIG. 4.
Figure 3:
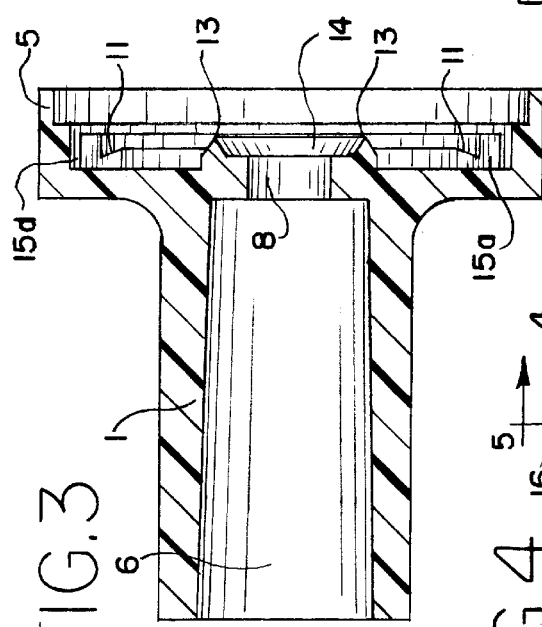
FIG. 3 is a sectional view taken along line 3—3 of FIG. 2.

One embodiment of a check valve suitable for use in medical techniques is shown in FIGS. 1–5. The check valve has a first hose connector housing 1 and a second hose connector housing 2. Between the two housings 1 and 2 there is provided a diaphragm disk 3 consisting of liquid silicone, silicone rubber or natural rubber. Although the check valve is especially suitable for the medical technique it can however be used in other suitable fluid applications.

A use in micro-pneumatic or micro-hydraulic applications is advantageously possible, too.

The hose connector housing 2 has an inner ring projection 4 and the hose connector housing 1 has an outer ring projection 5. Within the hose connector housing 1 further there is provided an entry space 6 and in the hose connector housing 2 there is provided an exit space 7. Both entry space 6 and exit space 7 are preferably generally cylindrical, with each having a decreasing diameter extending into the respective connector housing. Thus, in the preferred embodiment, entry space 6 decreases in the direction of fluid flow 17 to a smaller diameter and exit space 7 increases in the direction of fluid flow 17 to a larger diameter. In fluid communication with entry space 6 is an entry opening 8 of connector housing 1, opposite to which on the other side of the diaphragm disk 3 there is provided an exit opening 9 of connector housing 2, which in turn is in fluid communication with the exit space 7.

Diaphragm disk 3, preferably circular, is manufactured from liquid silicone, silicone rubber or natural rubber and is extremely elastic at normal temperatures and not sticky (due to the lack of electrostatic charge, for example). Diaphragm cross-section 3a is uniform and the thickness 3c is dependent on the needed opening pressure of the valve, and may range from 0.25 to 0.50 mm. The thickness tolerance may be controlled by the chosen manufacturing method of a sheet or mat consisting of liquid silicone, silicone rubber or natural rubber. Hardness of the diaphragm disk 3 is also dependent on the needed opening pressure of the valve, and may range between 40 and 70 degress Shore A. In its presently preferred form, diaphragm disk 3 is a circular piece of a medical grade silicone rubber material having a thickness of 0.3 mm and a durometer of approximately 40 degrees Shore A.

A valve space 10 is generally defined by joining the respective ends of connector housings 1, 2. The valve space 10 is generally separated by a ring-shaped seat 11 for the diaphragm provided on the first hose connector housing 1 and by a compression ring 12 provided on the second hose connector housing 2, wherein the diaphragm disk 3 is clamped between the above-mentioned parts. To this end, the diaphragm disk 3 with an annular margin 3b is positioned between the ring-shaped seat 11 of the diaphragm of the first connector housing 1 and the compression ring 12 of the second connector housing 2 in a sealing manner. This position is fixed by joining the two hose connector housings 1 and 2 together at the interface between the inner ring projection 4 and outer ring projection 5, which in turn clamps the annular margin 3b between ring-shaped seat 11, and compression ring 12. Such joinder may be executed by means of ultrasonic welding or use of medically approved adhesives (e.g. ultra-violet curing adhesives), or combination thereof. The presently preferred embodiment employs ultrasonic welding. The clamped interface between annular margin 3b, ring-shaped seat 11, and compression ring 12 may also be executed by means of ultrasonic welding or use of medically approved adhesives.

The valve space 10 on both sides of the diaphragm disk 3 is generally ring-shaped and is divided by the diaphragm disk 3 as long as the diaphragm 3 sealingly contacts a lip-shaped sealing ring 13 unitary with the connector housing 1. As long as in the entry space 6 there exists a suitable higher pressure than that in exit space 7, the diaphragm disk 3 is lifted away from the lip-shaped sealing ring 13 and the fluid streams through the entry opening 8, through a sealing lip central space 14, passing along the surface of the diaphragm disk 3, through a valve space passage 15a provided in ring-shaped seat 11, further through a generally annular bypass channel 18, and still further through a compression ring passage 16 into the other part of the valve space 10 and exit opening 9 (see FIG. 1, schematic membrane position 3d in phantom and tailed arrows depicting fluid flow in bottom half of figure). Of note is that annular bypass channel 18 allows ring-shaped seat valve space passage 15a and compression ring passage 16 to be angularly offset from one another (in contrast to the overlying relationship depicted in FIG. 1), and yet permit fluid communication therebetween. This design thus enhances the manufacturability of the valve and allows for automatic assembly thereof.

It is also of note that in the preferred embodiment, annular valve space passage 15b in combination with annular valve space passage 15d, forms the annular bypass channel 18 (see FIG. 1, upper half of figure, which is an axial cross-section perpendicular to the lower half of the figure as compression ring passage entrance 15c denotes). However, other combinations of valve space passages may be molded to form a generally annular bypass channel permitting fluid communication between valve space passage 15a and compression ring passage 16, such as utilizing only valve space passage 15d for this purpose or molding valve space passages 15b, 15d as discontinuous passages in each respective housing, but in combination with a mating housing forms a generally annular bypass channel that allows for fluid communication between the valve space 10 on both sides of diaphragm disk 3 under suitable pressure differential conditions.

In case the pressure in the exit space 7 should increase to be higher than the pressure in the entry space 6, which is not desired in the medical technique but can occur, then this pressure allows the disk 3 to contact the lip-shaped sealing ring 13 and thereby prevents passage of the fluid. This contact also occurs if the flow of the fluid stops, because of a lower inner radial tension of the diaphragm disk 3 in the area of the lip-shaped sealing ring 13 compared with the area of the ring-shaped seat 11 of the diaphragm, and thus the valve always has a tendency to be closed, and is closed without the appropriate level of overpressure present in entry space 6. These characteristics, however, only can be achieved by a diaphragm disk 3 being produced from die cut or stamped liquid silicone, silicone rubber or natural rubber.

In the preferred embodiment of the check valve, first and second connector housings 1, 2 are to be manufactured of polymeric materials that are generally medically accepted, e.g. polystyrenes, styrenic copolymers (A.B.S.) or polycarbonates. In particular, the preferred material is a styrenic copolymer (A.B.S.) manufactured by BASF Corporation, which is a methyl methacrylate, acrylonitrile/butadiene/styrene copolymer sold under the trademark name of Terlux 2802 TR. Although the diaphragm disk 3 may be between 10 and 40 mm in diameter, it is preferably about 10 mm and is die cut silicone rubber cut from a sheet or band.

The preferred connector housing 1 is configured as follows. Entry space 6 has an inner diameter that ranges from about 4.2 at the inlet to about 3.8 mm at the outlet, and the outlet communicates with entry opening 8 of diameter about 2.0 mm. The tip of the lip-shaped sealing ring 13, which engages the diaphragm disk 3 when the entry space 6 is not subjected to a suitable overpressure, has a diameter of about 3.6 mm. In radial dimensions (see FIG. 2), ring-shaped seat 11 has a beginning diameter of about 8.0 mm and terminates at a diameter of about 9.0 mm, which creates its first surface, at which point it rises axially to a second surface that is generally orthogonal to the housing axis and this surface extends to a diameter of about 10.0 mm (this second surface partially defines bypass channel 18). Outer ring projection 5 begins at a diameter of about 10.5 mm (thereby creating another surface that partially defines bypass channel 18), and has a first abutting surface orthagonal to the axis of connector housing 1 and this first abutting surface terminates at about a diameter of 11.3 mm. The outer diameter of the outer ring projection 5 is about 12.0 mm in diameter, and thus a second abutting surface orthagonal to the axis of connector housing 1 is formed that is approximately 0.7 mm. In axial longitudinal dimensions, and with reference from the datum of the second abutting surface orthagonal to the axis of first connector housing 1, i.e. the rightmost edge of the connector housing depicted in FIG. 3, the first abutting surface orthagonal to the axis of first connector housing 1 is approximately 0.8 mm. Further, and with respect to this datum, the second surface of ring-shaped seat 11 (generally orthagonal to the axis of first connector housing 1) is about 1.0 mm, and first surface of ring-shaped seat 11 begins at about 1.6 mm (which is at the greatest diameter in the radial direction for this surface), and terminates at a longitudinal axial dimension of 1.4 mm (which is at the smallest diameter). Further, and again with reference to this datum, the tip of the lip-shaped sealing ring 13 begins at about 1.1 mm. Further, and with reference again to this datum, sealing lip central space 14 terminates at an axial distance of about 1.9 mm, and the full length of connector housing 1 is about 12.6 mm. Still further, valve space passage 15a is about 1.0 mm wide as viewed in plan view, FIG. 2.

Figure 4:
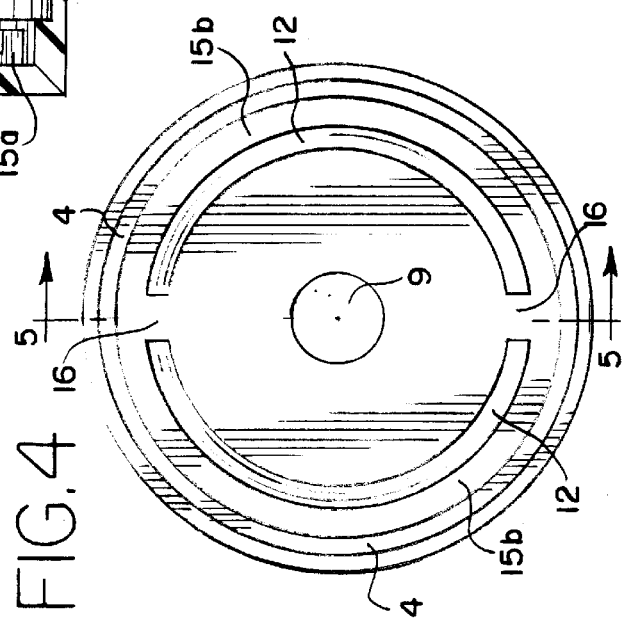
FIG. 4 is a plan view of an embodiment of a second hose connector housing of the present invention.

The preferred second hose connector housing 2 is configured as follows. In radial dimensions (see FIG. 4), exit opening 9 has a diameter of about 2.0 mm, compression ring 12 has an inner diameter of about 8.0 mm, and an outer diameter of about 9.0 mm. The inner ring projection 4 has an inner diameter of about 10.5 mm, thereby providing valve space passage 15b with an annular configuration, and inner ring projection 4 has an outer diameter of about 11.3 mm and thus also establishes a first abutting surface for inner ring projection 4 that is orthogonal to the axis of connector housing 2. Inner ring projection 4 coaxially transitions to a second abutting surface orthogonal to the axis of hose connector housing 2 and this surface terminates at a diameter of about 12.0 mm. Compression ring passage 16 is about 1.0 mm as viewed in plan view (FIG. 4). In axial longitudinal dimensions (see FIG. 5), and with reference to the datum of the leading edge of compression ring 12 (the leftmost edge as viewed in FIG. 5), the inner diameter of compression ring 12 terminates at an axial distance of about 0.30 mm, and compression ring passage 16, with reference to this datum, terminates at about 1.1 mm. Further, compression ring 12 extends about 1.4 mm to the surface of the second hose connector housing 2 that partially defines valve space 10 and is orthogonal to the axis of second connector housing 2. Also with reference to this datum, valve space passage 15b terminates at about 1.4 mm, and partially comprises the annular flow channel. Inner ring projection 4, with reference to the datum above, has a first abutting surface orthogonal to the axis of second connector housing 2 that is about 0.60 mm, and second abutting surface orthagonal to the axis of the second connector housing 2 is about 1.4 mm. The overall axial length of second connector housing 2 is about 12.4 mm.

It is of note that the above described check valve has numerous advantages. The disclosed check valve is of simple construction, yet provides a reliable check valve for operating pressures to which it is suited, for example, intravenous tube assemblies. It is of particular note that the disclosed assembly is economical to produce and yet provides a reliable check valve functionality. The construction is of particular benefit to automated assembly in that the disk diaphragm is clamped on its outer-circumference and opens and closes due to stretching of the clamped diaphragm disk resulting in a greater convex shape of the membrane (e.g., shape 3d) which creates an opening between the lip-shaped sealing ring 13 and the diaphragm disk 3. It is believed that in this check valve, only one set of dimensional tolerances, in particular the axial height differences between the tip of the lip-shaped sealing ring and the ring-shaped seat 11 need be closely evaluated to obtain a check valve of suitable functionality. Indeed with such a design it is believed that the tension in the membrane can be accurately predetermined to prevent a back flow (even at low flow rates of e.g. 0.15 milliliter per hour of liquid). In this manner, the present invention avoids complicated designs involving close tolerances of spherical radii and the like and thus lends itself to be readily assembled by automated equipment and yet result in reliably achieving the above-noted valve functionality.

While the preferred embodiment of this invention has been disclosed, it is to be understood that the invention is not limited to the disclosed example. Modifications discussed above, as well as in addition to those discussed, can be made without departing from the invention. For example, a configuration may be constructed in which a bypass channel may be in fluid communication with the valve space during forward fluid flow by way of a valve passage provided by a discontinuous ring-shaped seat angularly offset, with reference to the longitudinal axis of the valve, to a valve passage provided by a discontinuous compression ring. The scope of the invention is indicated in the appended claims, and all changes that come within the meaning and range of equivalency of the claims are therefore intended to be embraced therein. Thus, while the invention has been described with reference to a particular embodiment, modification of structure, material, and the like will be apparent to those skilled in the art, yet still fall within the scope of the invention.

What is claimed:

1. A check valve for the medical technique in a fluid pressure range from 0.1 to 0.02 bar comprising a first hose connector housing and a second hose connector housing, said first hose connector housing having a lip shaped sealing ring and a fluid entry space and said second hose connector housing having a compression ring (12) that defines a compression ring passage (16) and a fluid exit space, said first and second hose connectors joined together, and an imperforate diaphragm disk consisting of a flexible material positioned between the first and second hose connector housings, thereby forming a ring-shaped valve space (10) in the first hose connector housing and a generally annular bypass channel (18) around the circumference of said diaphragm disk (3), said diaphragm disk at an overpressure in the entry space is liftable from the lip-shaped sealing ring, whereby a flow cross-sectional area is created and said ring-shaped valve space (10) fluidly communicates with said compression ring passage (16) to permit fluid communication between said entry space and exit space of said first and second hose connector housings and which at an overpressure in the exit space said diaphragm disk is pressed onto the lip-shaped sealing ring to close the valve, wherein the circular diaphragm disk (3) is of a material selected from the group consisting of liquid silicone, silicone rubber or natural rubber and in that the thickness (3c) of the diaphragm cross-section (3a) is generally uniform.

2. A check valve according to claim 1, wherein the circular diaphragm disk (3) has a diameter of about 10 mm and a thickness (3c) of about 0.2 to 0.5 mm.

3. A check valve according to any of the claims 1 or 2, wherein the first hose connector housing includes a ring-shaped seat (11), the diaphragm disk (3) has an annular margin (3b) sealingly clamped between the ring-shaped seat (11) of the first hose connector housing (1) and the compression ring (12) of the second hose connector housing (2), and the first and the second hose connector housings (1, 2) consist of plastic and are welded to each other.

4. A check valve according to claim 1, wherein said second connector housing defines a ring shaped valve space thereby providing on each side of the diaphragm disk (3) a ring-shaped valve space (10), said first connector housing includes a ring-shaped seat (11), and a valve space passage (15a) therein whereby each ring-shaped valve space (10) fluidly communicates with the valve space passage (15a) and the compression ring passage (16) by the generally annular bypass channel (18) distributed around the circumference of the diaphragm disk (3).

5. A check valve according to claim 2, wherein said second connector housing defines a ring shaped valve space thereby providing on each side of the diaphragm disk (3) a ring-shaped valve space (10), said first connector housing includes a ring-shaped seat (11), and a valve space passage (15a) therein whereby each ring-shaped valve space (10) fluidly communicates with the valve space passage (15a) and the compression ring passage (16) by the generally annular bypass channel (18) distributed around the circumference of the diaphragm disk (3).

6. A check valve according to claim 1, wherein the first hose connector housing includes a ring-shaped seat (11) and valve space passage (15a) provided therein, said second hose connector housing defines a ring shaped valve space thereby providing on each side of the diaphragm disk (3) a ring-shaped valve space (10), whereby each ring-shaped valve space (10) fluidly communicates with the valve space passage (15a) and the compression ring passage (16) by the generally annular bypass channel (18) distributed around the circumference of the diaphragm disk (3), and the diaphragm disk (3) has an annular margin (3b) sealingly clamped between the ring-shaped seat (11) and the compression ring (12), with the first and second hose connector housings (1, 2) welded to each other.

7. A check valve according to claim 1, wherein diaphragm disk (3) is die cut from a sheet or mat of material selected from the group consisting of liquid silicone, silicone rubber, or natural rubber.

8. A check valve according to claim 2, wherein the diaphragm disk (3) is die cut from a sheet or mat of material selected from the group consisting of liquid silicone, silicone rubber, or natural rubber.

9. A check valve according to claim 3, wherein the diaphragm disk (3) is die cut from a sheet or mat of material selected from the group consisting of liquid silicone, silicone rubber, or natural rubber.

10. A check valve according to claim 4, wherein the diaphragm disk (3) is die cut from a sheet or mat of material selected from the group consisting of liquid silicone, silicone rubber, or natural rubber.

11. A check valve according to claim 5, wherein the diaphragm disk (3) is die cut from a sheet or mat of material selected from the group consisting of liquid silicone, silicone rubber, or natural rubber.

12. A check valve according to claim 6, wherein the diaphragm disk (3) is die cut from a sheet or mat of material selected from the group consisting of liquid silicone, silicone rubber, or natural rubber.

13. A check valve for use in medical techniques comprising:

a first hose connector housing (1) having a longitudinal axis and inlet passage for fluid flow (6), said first housing provided at an outboard end thereof with a first outer ring projection (5), a discontinuous ring-shaped seat (11) of lesser radius than said first outer ring projection (5), and a lip shaped sealing ring (13) of lesser radius than said ring-shaped seat (11), said lip shaped sealing ring (13) axially extending from said first connector housing (1) a greater distance than said ring-shaped seat (11);

a second hose connector housing (2) having a longitudinal axis and exit passage for fluid flow (7), said second housing provided at an outboard end thereof with a second outer ring projection (4), and a discontinuous compression ring (12) of lesser radius than said second outer ring projection (4) and axially extending from said second connector housing (2), and adapted to overly said ring-shaped seat (11);

an imperforate flexible diaphragm (3) overlying said lip shaped sealing ring (13) and disposed between said discontinuous ring-shaped seat (11) and said discontinuous compression ring (12);

means for sealing said first outer ring projection (5) with said second outer ring projection (4);

means for clamping said diaphragm (3) between said discontinuous ring-shaped seat (11) and said discontinuous compression ring (12) to provide in combination with said imperforate flexible diaphragm (3) and said ring-shaped seat (11) a sealing relationship therebetween when the fluid pressure is about equivalent in said inlet passage (6) and exit passage (7); and bypass channel means for fluid communication between said inlet passage (6) and outlet passage (7) when the fluid pressure in said inlet passage (6) is greater than the fluid pressure in said exit passage (7).

14. The check valve of claim 13, wherein said diaphragm is a disk of generally uniform thickness selected from the group consisting of liquid silicone, silicone rubber, or natural rubber.

15. The check valve of claim 13, wherein said disk is generally circular and a thickness of about 0.2 to 0.5 mm.

16. The check valve of claim 13, wherein said diaphragm is a generally circular body of uniform thickness die-cut from a sheet of material selected from the group consisting of liquid silicone, silicone rubber, or natural rubber.

17. The check valve of claim 13, wherein said diaphragm is a generally circular body of uniform thickness stamped from a flat mat of material selected from the group consisting of liquid silicone, silicone rubber, or natural rubber.

* * * * *